(12) United States Patent
Burnol et al.

(10) Patent No.: US 6,867,003 B1
(45) Date of Patent: Mar. 15, 2005

(54) GRB14, GRB14 FUSION PROTEINS, AND SCREENING METHODS

(75) Inventors: Anne-Françoise Burnol, Sevres (FR); Dominique Perdereau, Issy les Moulineaux (FR); Anne Kasus-Jacobi, Montigny le Bretonneux (FR); Véronique Bereziat, Palaiseau (FR); Jean Girard, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/936,697
(22) PCT Filed: Mar. 14, 2000
(86) PCT No.: PCT/FR00/00613

§ 371 (c)(1),
(2), (4) Date: Sep. 17, 2001

(87) PCT Pub. No.: WO00/55634

PCT Pub. Date: Sep. 21, 2000

(30) Foreign Application Priority Data

Mar. 15, 1999 (FR) .............................. 99 03159

(51) Int. Cl.[7] ........................ G01N 33/68; G01N 33/74; A61K 38/16; A61K 38/28
(52) U.S. Cl. ........................ 435/7.1; 435/7.2; 530/300; 530/324; 530/350
(58) Field of Search .................. 435/7.1, 7.2; 530/300, 530/324, 350

(56) References Cited

U.S. PATENT DOCUMENTS

| 5,726,027 A | 3/1998 | Olefsky ...................... 435/7.21 |
| 5,840,536 A | 11/1998 | Dunnington et al. ...... 435/69.1 |
| 5,889,150 A | 3/1999 | Schlessinger et al. ....... 530/350 |
| 6,465,623 B2 * | 10/2002 | Daly et al. ................ 530/388.1 |
| 2003/0044834 A1 * | 3/2003 | Daly et al. ...................... 435/6 |
| 2003/0129639 A1 * | 7/2003 | Daly et al. ...................... 435/6 |

FOREIGN PATENT DOCUMENTS

| WO | WO 96/34951 | * 11/1996 | ........... C12N/15/12 |
| WO | 98/01475 | 1/1998 | |

OTHER PUBLICATIONS

The American Heritage® Dictionary of the English Language, Fourth EditionCopyright © 2000 by Houghton Mifflin Company.*
Wells (Sep. 18, 1990) "Additivity of Mutational Effects in Proteins." Biochemistry 29(37): 8509–5817.*
Ngo et al. (Mar. 2, 1995) "The Protein Folding Problem and Tertiary Structure Prediction, Chapter 14: Computational Complexity Protein Structure Prediction, and the Levinthal Paradox" pp. 492–495.*
Bork (2000) "Powers and Pitfalls in Sequence Analysis: The 70% Hurdle." Genome Research 10:398–400.*
Skolnick and Fetrow (2000) "From gene to protein structure and function: novel applications of computational approaches in th genomic era." Trends in Biotech. 18(1): 34–39.*
Doerks et al., (Jun. 1998) "Protein annotation: detective work for function prediction." Trends in Genetics 14(6): 248–250.*
Smith and Zhang (Nov. 1997) "The challenges of genome sequence annotation or 'The devil is in the details'." Nature Biotechnology 15:1222–1223.*
Brenner (Apr. 1999) "Errors in genome annotation." Trends in Genetics 15(4): 132–133.*
Bork and Bairoch (Oct. 1996) "Go hunting in sequence databases but watch out for the traps." Trends in Genetics 12(10): 425–427.*
Dong et al. (Nov. 14, 1997) "Cloning, Chromosome Localization, Expression, and Characterization of an Src Homology 2 and Pleckstrin Homology Domain–containing Insulin Receptor Binding Protein hGrb10g." JBC 272(46): 29112–29112.*
Kasus–Jacobi et al. (Apr. 13, 2000) "Evidence for an interaction between the insulin receptor and Grb7. A role for two of its binding domains, PIR and SH2." Oncogene 19(16): 2052–2059.*
Han et al. (Oct. 1, 2001) "The Grb7 family proteins: structure, interactions with other signaling molecules and prudential cellular functions." Oncogene 20(44): 6315–6321.*
Stedman's Medical Dictionary 27th Edition.*
Béréziat et al. (Feb. 15, 2002) " Inhibition of Insulin Receptor Catalytic Activity by the Molecular Adapter Grb14." The Journ of Biological Chemistry 277(7): 4845–4852.*
Daly, R. et al. Cloning and Characterization of Grb14, A Novel Member of the Grb7 Gene Family (1996) *Jour. of Biol. Chem.* 271(21):12502–12510.
Frantz, U. et al. Human Grb–IRβ/Grb10. (*1997*)*Jour. of Biol. Chem.* 272(5): 2659–2667.
He, et al. Grb10 Interacts Differentially with the Insulin Receptor, Insulin–Like Growth Factor I Receptor, and Epidermal Growth Factor Receptor via The Grb10 Src Homology 2 (SH2) Domain and a Second Novel Domain Located Between The Pleckstrin Homology and SH2 Domains. (1998) *Jour. of Biol. Chem., 273 (12): 6860–6867.*
Kasus–Jacobi, A. et al. Identification of The Rat Adapter Grb14 as an Inhibitor of Insulin Actions (1998) *Jour. of Biol. Chem. 273 (40):26026–26035.*

(List continued on next page.)

Primary Examiner—Brenda Brumback
Assistant Examiner—Christopher James Nichols
(74) Attorney, Agent, or Firm—Morgan Lewis & Bockius LLP

(57) ABSTRACT

The invention concerns the use of Grb14 and homologous adapting proteins, as tool for screening molecules designed for the treatment of diseases involving insulin. The invention also concerns a method for detecting molecules capable of modulating the tyrosine kinase activity of the insulin receptor.

6 Claims, 7 Drawing Sheets

OTHER PUBLICATIONS

Figure 1:
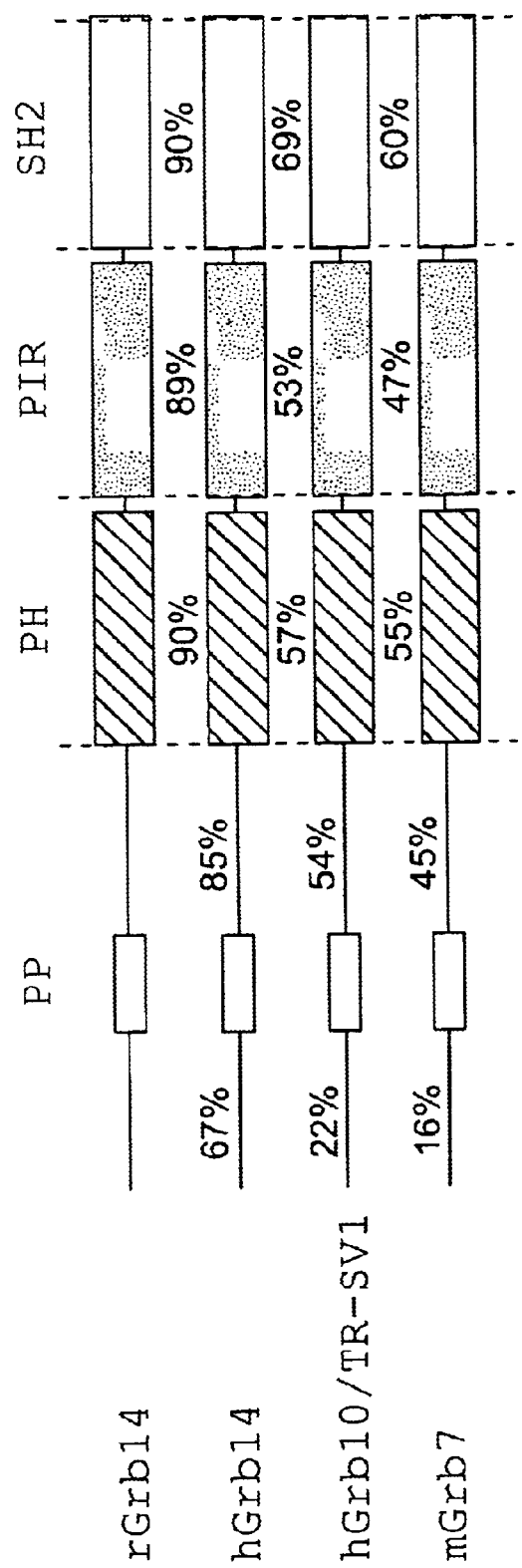

Liu. et al. Grb–IR: A SH2–Domain–Containing Protein That Binds To The Insulin Receptor and Inhibits Its Function (1995) *Proc. Natl. Acad. Sci. USA, 92:10287–10291.*

O'Neill. et al. Interaction of A Grb–IR Splice Variant (A Human Grb10 Homolog) with The Insulin and Insulin–Like Growth Factor I Receptors (1996) *Jour. of Biol. Chem., 271 (37): 22506–22513.*

* cited by examiner

```
                            365                                    407                                      436
rGrb14       353 QARSACSSQS-VSPMRSVSENSLVAMDFSGQKTRVIDNPTEALSVAVEEGLAWRKKGCLRLGNHGSPTAPSQSSAVNMALHRSQP
hGrb14       353 QGRSGCSSQS-ISPMRSTSENSLVAMDFSGQKSRVIENPTEALSVAVEEGLAWRKKGCLRLGTHGSPTASSQSSATNMAIHRSQP
h Grb10/IR-SV1 353 QQRKALLSPF-STPVRSVSENSLVAMDFSGQTGRVIENPAEAQSAALEEGHAWRKR-STRMNILGS-QSPLHPSTLSTVIHRTQH
h Grb14      354 -SRHLHPSCLGSPPLRSASDNTIVAMDFSGHAGRVIENPREALSVALEEAQAWRKKTNHRLSLPMP----ASGTSLSAATHRTQL
                  *   *  *       **  ***** *   *****   * **  ****  *   ****     *   *                **  *
```

FIG. 2

PIR-SH2 DOMANIS:

rGrb14

QARSACSSQSVSPMRSVSENSLVAMDFSGQKTRVIDNPTEALSVAVEEGLAWRKKGC
LRLGNHGSPTAPSQSSAVNMALHRSQPWEHHRISRDEAQQLITRQGPVDGVFLVRDS
QSNPRTFVLSMSHGQKIKHFQIIPVEDDGEVFHTLDDGHTKFTDLIQLVEFYQLNKG
VLPCKLKHYCARMAV hGrb10

QQRKALLSPFSTPVRSVSENSLVAMDFSGQTGRVIENPAEAQSAALEEGHAWRKRST
RMNILGSQSPLHPSTLSTVIHRTQHWFHGRFSREESHRIIKQQGLVDGLFLLRDSQS
NPKAFVLTLCHHQKIKNFQILPCEDDGQTFFSLDDGNTKFSDLIQLVDFYQLNKGVL
PCKLKHHCIRVAL hGrb7

SRHLHPSCLGSPPLRSAASDNTLVAMDFSGHAGRVIENPREALSVALEEAQAWRKKTN
HRLSLPMPASGTSLSAAIHRTQLWFHGRISREESQRLIGQQGLVDGLFLVRESQRNP
QGFVLSLCHLQKVKHYLILPSEEEGRLYFSMDDGQTRFTDLLQLVEFHQLNRGICLL
RHCCTRVAL

FIG. 3

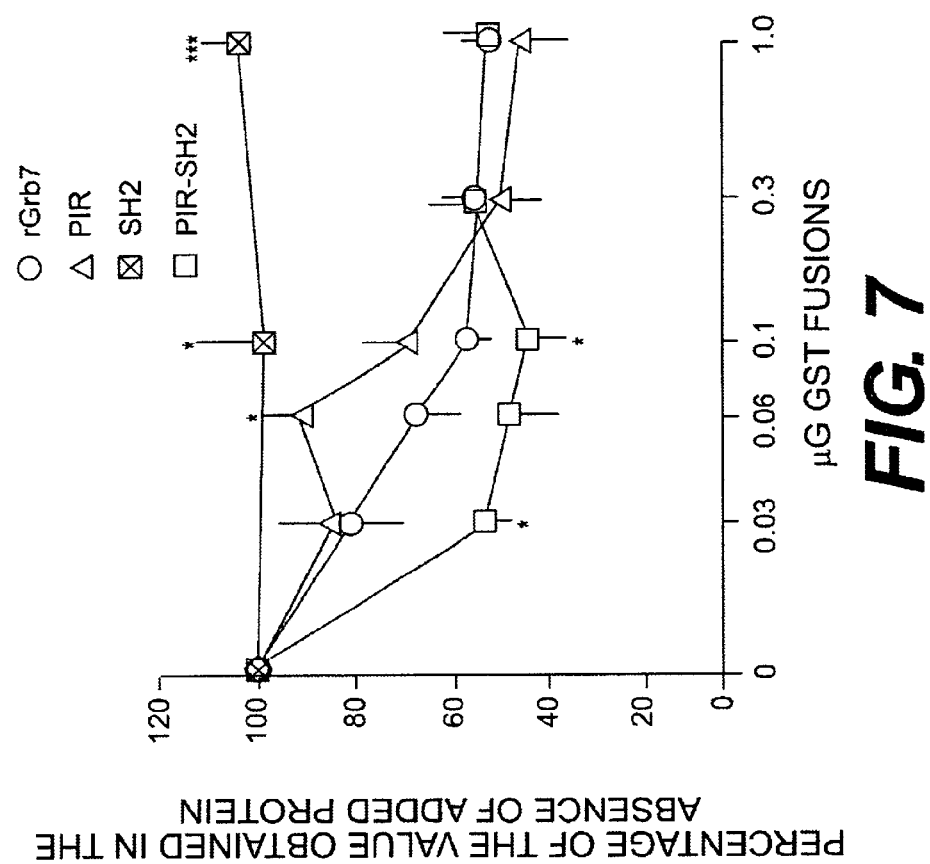

SEQUENCE LISTING

```
<160> NUMBER OF SEQ ID NOS: 28

<210> SEQ ID NO 1
<211> LENGTH: 43
<212> TYPE: PRT
<213> ORGANISM: Rattus sp.

<400> SEQUENCE: 1

Pro Met Arg Ser Val Ser Glu Asn Ser Leu Val Ala Met Asp Phe Ser
 1               5                  10                  15

Gly Gln Lys Thr Arg Val Ile Asp Asn Pro Thr Glu Ala Leu Ser Val
            20                  25                  30

Ala Val Glu Glu Gly Leu Ala Trp Arg Lys Lys
        35                  40

<210> SEQ ID NO 2
<211> LENGTH: 84
<212> TYPE: PRT
<213> ORGANISM: Rattus sp.

<400> SEQUENCE: 2

Gln Ala Arg Ser Ala Cys Ser Ser Gln Ser Val Ser Pro Met Arg Ser
 1               5                  10                  15
```

-continued

Val Ser Glu Asn Ser Leu Val Ala Met Asp Phe Ser Gly Gln Lys Thr
            20                  25                  30

Arg Val Ile Asp Asn Pro Thr Glu Ala Leu Ser Val Ala Val Glu Glu
        35                  40                  45

Gly Leu Ala Trp Arg Lys Lys Gly Cys Leu Arg Leu Gly Asn His Gly
    50                  55                  60

Ser Pro Thr Ala Pro Ser Gln Ser Ser Ala Val Asn Met Ala Leu His
65                  70                  75                  80

Arg Ser Gln Pro

<210> SEQ ID NO 3
<211> LENGTH: 174
<212> TYPE: PRT
<213> ORGANISM: Rattus sp.

<400> SEQUENCE: 3

Pro Met Arg Ser Val Ser Glu Asn Ser Leu Val Ala Met Asp Phe Ser
1               5                   10                  15

Gly Gln Lys Thr Arg Val Ile Asp Asn Pro Thr Glu Ala Leu Ser Val
            20                  25                  30

Ala Val Glu Glu Gly Leu Ala Trp Arg Lys Lys Gly Cys Leu Arg Leu
        35                  40                  45

Gly Asn His Gly Ser Pro Thr Ala Pro Ser Gln Ser Ser Ala Val Asn
    50                  55                  60

Met Ala Leu His Arg Ser Gln Pro Trp Phe His His Arg Ile Ser Arg
65                  70                  75                  80

Asp Glu Ala Gln Gln Leu Ile Thr Arg Gln Gly Pro Val Asp Gly Val
                85                  90                  95

Phe Leu Val Arg Asp Ser Gln Ser Asn Pro Arg Thr Phe Val Leu Ser
                100                 105                 110

Met Ser His Gly Gln Lys Ile Lys His Phe Gln Ile Ile Pro Val Glu
            115                 120                 125

Asp Asp Gly Glu Val Phe His Thr Leu Asp Asp Gly His Thr Lys Phe
        130                 135                 140

Thr Asp Leu Ile Gln Leu Val Glu Phe Tyr Gln Leu Asn Lys Gly Val
145                 150                 155                 160

Leu Pro Cys Lys Leu Lys His Tyr Cys Ala Arg Met Ala Val
                165                 170

<210> SEQ ID NO 4
<211> LENGTH: 186
<212> TYPE: PRT
<213> ORGANISM: Rattus sp.

<400> SEQUENCE: 4

Gln Ala Arg Ser Ala Cys Ser Ser Gln Ser Val Ser Pro Met Arg Ser
1               5                   10                  15

Val Ser Glu Asn Ser Leu Val Ala Met Asp Phe Ser Gly Gln Lys Thr
            20                  25                  30

Arg Val Ile Asp Asn Pro Thr Glu Ala Leu Ser Val Ala Val Glu Glu
        35                  40                  45

Gly Leu Ala Trp Arg Lys Lys Gly Cys Leu Arg Leu Gly Asn His Gly
    50                  55                  60

Ser Pro Thr Ala Pro Ser Gln Ser Ser Ala Val Asn Met Ala Leu His
65                  70                  75                  80

Arg Ser Gln Pro Trp Phe His His Arg Ile Ser Arg Asp Glu Ala Gln

```
                     85                  90                  95
Gln Leu Ile Thr Arg Gln Gly Pro Val Asp Gly Val Phe Leu Val Arg
            100                 105                 110
Asp Ser Gln Ser Asn Pro Arg Thr Phe Val Leu Ser Met Ser His Gly
        115                 120                 125
Gln Lys Ile Lys His Phe Gln Ile Ile Pro Val Glu Asp Asp Gly Glu
    130                 135                 140
Val Phe His Thr Leu Asp Asp Gly His Thr Lys Phe Thr Asp Leu Ile
145                 150                 155                 160
Gln Leu Val Glu Phe Tyr Gln Leu Asn Lys Gly Val Leu Pro Cys Lys
                165                 170                 175
Leu Lys His Tyr Cys Ala Arg Met Ala Val
                180                 185

<210> SEQ ID NO 5
<211> LENGTH: 43
<212> TYPE: PRT
<213> ORGANISM: Homo sapiens

<400> SEQUENCE: 5

Pro Met Arg Ser Ile Ser Glu Asn Ser Leu Val Ala Met Asp Phe Ser
 1               5                  10                  15
Gly Gln Lys Ser Arg Val Ile Glu Asn Pro Thr Glu Ala Leu Ser Val
            20                  25                  30
Ala Val Glu Glu Gly Leu Ala Trp Arg Lys Lys
        35                  40

<210> SEQ ID NO 6
<211> LENGTH: 84
<212> TYPE: PRT
<213> ORGANISM: Homo sapiens

<400> SEQUENCE: 6

Gln Gly Arg Ser Gly Cys Ser Ser Gln Ser Ile Ser Pro Met Arg Ser
 1               5                  10                  15
Ile Ser Glu Asn Ser Leu Val Ala Met Asp Phe Ser Gly Gln Lys Ser
            20                  25                  30
Arg Val Ile Glu Asn Pro Thr Glu Ala Leu Ser Val Ala Val Glu Glu
        35                  40                  45
Gly Leu Ala Trp Arg Lys Lys Gly Cys Leu Arg Leu Gly Thr His Gly
    50                  55                  60
Ser Pro Thr Ala Ser Ser Gln Ser Ser Ala Thr Asn Met Ala Ile His
65                  70                  75                  80
Arg Ser Gln Pro

<210> SEQ ID NO 7
<211> LENGTH: 174
<212> TYPE: PRT
<213> ORGANISM: Homo sapiens

<400> SEQUENCE: 7

Pro Met Arg Ser Ile Ser Glu Asn Ser Leu Val Ala Met Asp Phe Ser
 1               5                  10                  15
Gly Gln Lys Ser Arg Val Ile Glu Asn Pro Thr Glu Ala Leu Ser Val
            20                  25                  30
Ala Val Glu Glu Gly Leu Ala Trp Arg Lys Lys Gly Cys Leu Arg Leu
        35                  40                  45
```

-continued

```
Gly Thr His Gly Ser Pro Thr Ala Ser Ser Gln Ser Ser Ala Thr Asn
            50                  55                  60

Met Ala Ile His Arg Ser Gln Pro Trp Phe His His Lys Ile Ser Arg
 65                  70                  75                  80

Asp Glu Ala Gln Arg Leu Ile Ile Gln Gln Gly Leu Val Asp Gly Val
                 85                  90                  95

Phe Leu Val Arg Asp Ser Gln Ser Asn Pro Lys Thr Phe Val Leu Ser
                100                 105                 110

Met Ser His Gly Gln Lys Ile Lys His Phe Gln Ile Ile Pro Val Glu
            115                 120                 125

Asp Asp Gly Glu Met Phe His Thr Leu Asp Asp Gly His Thr Arg Phe
130                 135                 140

Thr Asp Leu Ile Gln Leu Val Glu Phe Tyr Gln Leu Asn Lys Gly Val
145                 150                 155                 160

Leu Pro Cys Lys Leu Lys His Tyr Cys Ala Arg Ile Ala Leu
                165                 170
```

<210> SEQ ID NO 8
<211> LENGTH: 186
<212> TYPE: PRT
<213> ORGANISM: Homo sapiens

<400> SEQUENCE: 8

```
Gln Gly Arg Ser Gly Cys Ser Ser Gln Ser Ile Ser Pro Met Arg Ser
  1               5                  10                  15

Ile Ser Glu Asn Ser Leu Val Ala Met Asp Phe Ser Gly Gln Lys Ser
             20                  25                  30

Arg Val Ile Glu Asn Pro Thr Glu Ala Leu Ser Val Ala Val Glu Glu
         35                  40                  45

Gly Leu Ala Trp Arg Lys Lys Gly Cys Leu Arg Leu Gly Thr His Gly
     50                  55                  60

Ser Pro Thr Ala Ser Ser Gln Ser Ser Ala Thr Asn Met Ala Ile His
 65                  70                  75                  80

Arg Ser Gln Pro Trp Phe His His Lys Ile Ser Arg Asp Glu Ala Gln
                 85                  90                  95

Arg Leu Ile Ile Gln Gln Gly Leu Val Asp Gly Val Phe Leu Val Arg
                100                 105                 110

Asp Ser Gln Ser Asn Pro Lys Thr Phe Val Leu Ser Met Ser His Gly
            115                 120                 125

Gln Lys Ile Lys His Phe Gln Ile Ile Pro Val Glu Asp Asp Gly Glu
        130                 135                 140

Met Phe His Thr Leu Asp Asp Gly His Thr Arg Phe Thr Asp Leu Ile
145                 150                 155                 160

Gln Leu Val Glu Phe Tyr Gln Leu Asn Lys Gly Val Leu Pro Cys Lys
                165                 170                 175

Leu Lys His Tyr Cys Ala Arg Ile Ala Leu
            180                 185
```

<210> SEQ ID NO 9
<211> LENGTH: 43
<212> TYPE: PRT
<213> ORGANISM: mus muris

<400> SEQUENCE: 9

```
Pro Met Arg Ser Val Ser Glu Asn Ser Leu Val Ala Met Asp Phe Ser
  1               5                  10                  15
```

Gly Gln Ile Gly Arg Val Ile Asp Asn Pro Ala Glu Ala Gln Ser Ala
                20                  25                  30

Ala Leu Glu Glu Gly His Ala Trp Arg Asn Gly
            35                  40

<210> SEQ ID NO 10
<211> LENGTH: 82
<212> TYPE: PRT
<213> ORGANISM: mus muris

<400> SEQUENCE: 10

Pro Gln Arg Lys Gly Leu Pro Pro Phe Asn Ala Pro Met Arg Ser
1               5                   10                  15

Val Ser Glu Asn Ser Leu Val Ala Met Asp Phe Ser Gly Gln Ile Gly
                20                  25                  30

Arg Val Ile Asp Asn Pro Ala Glu Ala Gln Ser Ala Ala Leu Glu Glu
                35                  40                  45

Gly His Ala Trp Arg Asn Gly Ser Thr Arg Met Asn Ile Leu Ser Ser
            50                  55                  60

Gln Ser Pro Leu His Pro Ser Thr Leu Asn Ala Val Ile His Arg Thr
65                  70                  75                  80

Gln His

<210> SEQ ID NO 11
<211> LENGTH: 172
<212> TYPE: PRT
<213> ORGANISM: mus muris

<400> SEQUENCE: 11

Pro Met Arg Ser Val Ser Glu Asn Ser Leu Val Ala Met Asp Phe Ser
1               5                   10                  15

Gly Gln Ile Gly Arg Val Ile Asp Asn Pro Ala Glu Ala Gln Ser Ala
                20                  25                  30

Ala Leu Glu Glu Gly His Ala Trp Arg Asn Gly Ser Thr Arg Met Asn
            35                  40                  45

Ile Leu Ser Ser Gln Ser Pro Leu His Pro Ser Thr Leu Asn Ala Val
        50                  55                  60

Ile His Arg Thr Gln His Trp Phe His Gly Arg Ile Ser Arg Glu Glu
65                  70                  75                  80

Ser His Arg Ile Ile Lys Gln Gln Gly Leu Val Asp Gly Leu Phe Leu
                85                  90                  95

Leu Arg Asp Ser Gln Ser Asn Pro Lys Ala Phe Val Leu Thr Leu Cys
                100                 105                 110

His His Gln Lys Ile Lys Asn Phe Gln Ile Leu Pro Cys Glu Asp Asp
            115                 120                 125

Gly Gln Thr Phe Phe Thr Leu Asp Asp Gly Asn Thr Lys Phe Ser Asp
        130                 135                 140

Leu Ile Gln Leu Val Asp Phe Tyr Gln Leu Asn Lys Gly Val Leu Pro
145                 150                 155                 160

Cys Lys Leu Lys His His Cys Ile Arg Val Ala Leu
                165                 170

<210> SEQ ID NO 12
<211> LENGTH: 184
<212> TYPE: PRT
<213> ORGANISM: mus muris

<400> SEQUENCE: 12

-continued

Pro Gln Arg Lys Gly Leu Pro Pro Phe Asn Ala Pro Met Arg Ser
1               5                   10                  15

Val Ser Glu Asn Ser Leu Val Ala Met Asp Phe Ser Gly Gln Ile Gly
                20                  25                  30

Arg Val Ile Asp Asn Pro Ala Glu Ala Gln Ser Ala Ala Leu Glu Glu
            35                  40                  45

Gly His Ala Trp Arg Asn Gly Ser Thr Arg Met Asn Ile Leu Ser Ser
        50                  55                  60

Gln Ser Pro Leu His Pro Ser Thr Leu Asn Ala Val Ile His Arg Thr
65                  70                  75                  80

Gln His Trp Phe His Gly Arg Ile Ser Arg Glu Ser His Arg Ile
                85                  90                  95

Ile Lys Gln Gln Gly Leu Val Asp Gly Leu Phe Leu Arg Asp Ser
            100                 105                 110

Gln Ser Asn Pro Lys Ala Phe Val Leu Thr Leu Cys His His Gln Lys
        115                 120                 125

Ile Lys Asn Phe Gln Ile Leu Pro Cys Glu Asp Gly Gln Thr Phe
    130                 135                 140

Phe Thr Leu Asp Asp Gly Asn Thr Lys Phe Ser Asp Leu Ile Gln Leu
145                 150                 155                 160

Val Asp Phe Tyr Gln Leu Asn Lys Gly Val Leu Pro Cys Lys Leu Lys
                165                 170                 175

His His Cys Ile Arg Val Ala Leu
            180

<210> SEQ ID NO 13
<211> LENGTH: 43
<212> TYPE: PRT
<213> ORGANISM: Homo sapiens

<400> SEQUENCE: 13

Pro Val Arg Ser Val Ser Glu Asn Ser Leu Val Ala Met Asp Phe Ser
1               5                   10                  15

Gly Gln Thr Gly Arg Val Ile Glu Asn Pro Ala Glu Ala Gln Ser Ala
                20                  25                  30

Ala Leu Glu Glu Gly His Ala Trp Arg Lys Arg
            35                  40

<210> SEQ ID NO 14
<211> LENGTH: 82
<212> TYPE: PRT
<213> ORGANISM: Homo sapiens

<400> SEQUENCE: 14

Gln Gln Arg Lys Ala Leu Leu Ser Pro Phe Ser Thr Pro Val Arg Ser
1               5                   10                  15

Val Ser Glu Asn Ser Leu Val Ala Met Asp Phe Ser Gly Gln Thr Gly
                20                  25                  30

Arg Val Ile Glu Asn Pro Ala Glu Ala Gln Ser Ala Ala Leu Glu Glu
            35                  40                  45

Gly His Ala Trp Arg Lys Arg Ser Thr Arg Met Asn Ile Leu Gly Ser
        50                  55                  60

Gln Ser Pro Leu His Pro Ser Thr Leu Ser Thr Val Ile His Arg Thr
65                  70                  75                  80

Gln His

```
<210> SEQ ID NO 15
<211> LENGTH: 172
<212> TYPE: PRT
<213> ORGANISM: Homo sapiens

<400> SEQUENCE: 15

Pro Val Arg Ser Val Ser Glu Asn Ser Leu Val Ala Met Asp Phe Ser
  1               5                  10                  15

Gly Gln Thr Gly Arg Val Ile Glu Asn Pro Ala Glu Ala Gln Ser Ala
                 20                  25                  30

Ala Leu Glu Glu Gly His Ala Trp Arg Lys Arg Ser Thr Arg Met Asn
             35                  40                  45

Ile Leu Gly Ser Gln Ser Pro Leu His Pro Ser Thr Leu Ser Thr Val
         50                  55                  60

Ile His Arg Thr Gln His Trp Phe His Gly Arg Phe Ser Arg Glu Glu
 65                  70                  75                  80

Ser His Arg Ile Ile Lys Gln Gln Gly Leu Val Asp Gly Leu Phe Leu
                 85                  90                  95

Leu Arg Asp Ser Gln Ser Asn Pro Lys Ala Phe Val Leu Thr Leu Cys
            100                 105                 110

His His Gln Lys Ile Lys Asn Phe Gln Ile Leu Pro Cys Glu Asp Asp
        115                 120                 125

Gly Gln Thr Phe Phe Ser Leu Asp Asp Gly Asn Thr Lys Phe Ser Asp
    130                 135                 140

Leu Ile Gln Leu Val Asp Phe Tyr Gln Leu Asn Lys Gly Val Leu Pro
145                 150                 155                 160

Cys Lys Leu Lys His His Cys Ile Arg Val Ala Leu
                165                 170

<210> SEQ ID NO 16
<211> LENGTH: 184
<212> TYPE: PRT
<213> ORGANISM: Homo sapiens

<400> SEQUENCE: 16

Gln Gln Arg Lys Ala Leu Leu Ser Pro Phe Ser Thr Pro Val Arg Ser
  1               5                  10                  15

Val Ser Glu Asn Ser Leu Val Ala Met Asp Phe Ser Gly Gln Thr Gly
                 20                  25                  30

Arg Val Ile Glu Asn Pro Ala Glu Ala Gln Ser Ala Ala Leu Glu Glu
             35                  40                  45

Gly His Ala Trp Arg Lys Arg Ser Thr Arg Met Asn Ile Leu Gly Ser
         50                  55                  60

Gln Ser Pro Leu His Pro Ser Thr Leu Ser Thr Val Ile His Arg Thr
 65                  70                  75                  80

Gln His Trp Phe His Gly Arg Phe Ser Arg Glu Glu Ser His Arg Ile
                 85                  90                  95

Ile Lys Gln Gln Gly Leu Val Asp Gly Leu Phe Leu Leu Arg Asp Ser
            100                 105                 110

Gln Ser Asn Pro Lys Ala Phe Val Leu Thr Leu Cys His His Gln Lys
        115                 120                 125

Ile Lys Asn Phe Gln Ile Leu Pro Cys Glu Asp Asp Gly Gln Thr Phe
    130                 135                 140

Phe Ser Leu Asp Asp Gly Asn Thr Lys Phe Ser Asp Leu Ile Gln Leu
145                 150                 155                 160
```

-continued

```
Val Asp Phe Tyr Gln Leu Asn Lys Gly Val Leu Pro Cys Lys Leu Lys
                165                 170                 175

His His Cys Ile Arg Val Ala Leu
            180

<210> SEQ ID NO 17
<211> LENGTH: 43
<212> TYPE: PRT
<213> ORGANISM: Rattus sp.

<400> SEQUENCE: 17

Pro Leu Arg Ser Val Ser Asp Asn Thr Leu Val Ala Met Asp Phe Ser
  1               5                  10                  15

Gly His Ala Gly Arg Val Ile Asp Asn Pro Arg Glu Ala Leu Ser Ala
                 20                  25                  30

Ala Met Glu Glu Ala Gln Ala Trp Arg Lys Lys
             35                  40

<210> SEQ ID NO 18
<211> LENGTH: 80
<212> TYPE: PRT
<213> ORGANISM: Rattus sp.

<400> SEQUENCE: 18

Ser Arg His Leu Arg Leu Ser Tyr Leu Gly Ser Pro Pro Leu Arg Ser
  1               5                  10                  15

Val Ser Asp Asn Thr Leu Val Ala Met Asp Phe Ser Gly His Ala Gly
                 20                  25                  30

Arg Val Ile Asp Asn Pro Arg Glu Ala Leu Ser Ala Ala Met Glu Glu
             35                  40                  45

Ala Gln Ala Trp Arg Lys Lys Thr Asn His Arg Leu Ser Leu Pro Thr
         50                  55                  60

Thr Cys Ser Gly Ser Ser Leu Ser Ala Ala Ile His Arg Thr Gln Pro
 65                  70                  75                  80

<210> SEQ ID NO 19
<211> LENGTH: 170
<212> TYPE: PRT
<213> ORGANISM: Rattus sp.

<400> SEQUENCE: 19

Pro Leu Arg Ser Val Ser Asp Asn Thr Leu Val Ala Met Asp Phe Ser
  1               5                  10                  15

Gly His Ala Gly Arg Val Ile Asp Asn Pro Arg Glu Ala Leu Ser Ala
                 20                  25                  30

Ala Met Glu Glu Ala Gln Ala Trp Arg Lys Lys Thr Asn His Arg Leu
             35                  40                  45

Ser Leu Pro Thr Thr Cys Ser Gly Ser Ser Leu Ser Ala Ala Ile His
         50                  55                  60

Arg Thr Gln Pro Trp Phe His Gly Arg Ile Ser Arg Glu Glu Ser Gln
 65                  70                  75                  80

Arg Leu Ile Gly Gln Gln Gly Leu Val Asp Gly Val Phe Leu Val Arg
                 85                  90                  95

Glu Ser Gln Arg Asn Pro Gln Gly Phe Val Leu Ser Leu Cys His Leu
                100                 105                 110

Gln Lys Val Lys His Tyr Leu Ile Leu Pro Ser Glu Asp Glu Gly Cys
            115                 120                 125

Leu Tyr Phe Ser Met Asp Glu Gly Gln Thr Arg Phe Thr Asp Leu Leu
```

```
                130             135             140
Gln Leu Val Glu Phe His Gln Leu Asn Arg Gly Ile Leu Pro Cys Leu
145                 150                 155                 160

Leu Arg His Cys Cys Ala Arg Val Ala Leu
                165                 170
```

<210> SEQ ID NO 20
<211> LENGTH: 182
<212> TYPE: PRT
<213> ORGANISM: Rattus sp.

<400> SEQUENCE: 20

```
Ser Arg His Leu Arg Leu Ser Tyr Leu Gly Ser Pro Pro Leu Arg Ser
1               5                   10                  15

Val Ser Asp Asn Thr Leu Val Ala Met Asp Phe Ser Gly His Ala Gly
                20                  25                  30

Arg Val Ile Asp Asn Pro Arg Glu Ala Leu Ser Ala Ala Met Glu Glu
            35                  40                  45

Ala Gln Ala Trp Arg Lys Lys Thr Asn His Arg Leu Ser Leu Pro Thr
        50                  55                  60

Thr Cys Ser Gly Ser Ser Leu Ser Ala Ala Ile His Arg Thr Gln Pro
65                  70                  75                  80

Trp Phe His Gly Arg Ile Ser Arg Glu Glu Ser Gln Arg Leu Ile Gly
                85                  90                  95

Gln Gln Gly Leu Val Asp Gly Val Phe Leu Val Arg Glu Ser Gln Arg
                100                 105                 110

Asn Pro Gln Gly Phe Val Leu Ser Leu Cys His Leu Gln Lys Val Lys
            115                 120                 125

His Tyr Leu Ile Leu Pro Ser Glu Asp Glu Gly Cys Leu Tyr Phe Ser
        130                 135                 140

Met Asp Glu Gly Gln Thr Arg Phe Thr Asp Leu Leu Gln Leu Val Glu
145                 150                 155                 160

Phe His Gln Leu Asn Arg Gly Ile Leu Pro Cys Leu Arg His Cys
                165                 170                 175

Cys Ala Arg Val Ala Leu
                180
```

<210> SEQ ID NO 21
<211> LENGTH: 43
<212> TYPE: PRT
<213> ORGANISM: Homo sapiens

<400> SEQUENCE: 21

```
Pro Leu Arg Ser Ala Ser Asp Asn Thr Leu Val Ala Met Asp Phe Ser
1               5                   10                  15

Gly His Ala Gly Arg Val Ile Glu Asn Pro Arg Glu Ala Leu Ser Val
                20                  25                  30

Ala Leu Glu Glu Ala Gln Ala Trp Arg Lys Lys
            35                  40
```

<210> SEQ ID NO 22
<211> LENGTH: 80
<212> TYPE: PRT
<213> ORGANISM: Homo sapiens

<400> SEQUENCE: 22

```
Ser Arg His Leu His Pro Ser Cys Leu Gly Ser Pro Pro Leu Arg Ser
1               5                   10                  15
```

-continued

```
Ala Ser Asp Asn Thr Leu Val Ala Met Asp Phe Ser Gly His Ala Gly
             20                  25                  30

Arg Val Ile Glu Asn Pro Arg Glu Ala Leu Ser Val Ala Leu Glu Glu
         35                  40                  45

Ala Gln Ala Trp Arg Lys Lys Thr Asn His Arg Leu Ser Leu Pro Met
     50                  55                  60

Pro Ala Ser Gly Thr Ser Leu Ser Ala Ala Ile His Arg Thr Gln Leu
 65                  70                  75                  80
```

<210> SEQ ID NO 23
<211> LENGTH: 170
<212> TYPE: PRT
<213> ORGANISM: Homo sapiens

<400> SEQUENCE: 23

```
Pro Leu Arg Ser Ala Ser Asp Asn Thr Leu Val Ala Met Asp Phe Ser
 1               5                  10                  15

Gly His Ala Gly Arg Val Ile Glu Asn Pro Arg Glu Ala Leu Ser Val
             20                  25                  30

Ala Leu Glu Glu Ala Gln Ala Trp Arg Lys Lys Thr Asn His Arg Leu
         35                  40                  45

Ser Leu Pro Met Pro Ala Ser Gly Thr Ser Leu Ser Ala Ala Ile His
     50                  55                  60

Arg Thr Gln Leu Trp Phe His Gly Arg Ile Ser Arg Glu Glu Ser Gln
 65                  70                  75                  80

Arg Leu Ile Gly Gln Gln Gly Leu Val Asp Gly Leu Phe Leu Val Arg
                 85                  90                  95

Glu Ser Gln Arg Asn Pro Gln Gly Phe Val Leu Ser Leu Cys His Leu
                100                 105                 110

Gln Lys Val Lys His Tyr Leu Ile Leu Pro Ser Glu Glu Gly Arg
             115                 120                 125

Leu Tyr Phe Ser Met Asp Asp Gly Gln Thr Arg Phe Thr Asp Leu Leu
         130                 135                 140

Gln Leu Val Glu Phe His Gln Leu Asn Arg Gly Ile Leu Pro Cys Leu
145                 150                 155                 160

Leu Arg His Cys Cys Thr Arg Val Ala Leu
                165                 170
```

<210> SEQ ID NO 24
<211> LENGTH: 182
<212> TYPE: PRT
<213> ORGANISM: Homo sapiens

<400> SEQUENCE: 24

```
Ser Arg His Leu His Pro Ser Cys Leu Gly Ser Pro Leu Arg Ser
 1               5                  10                  15

Ala Ser Asp Asn Thr Leu Val Ala Met Asp Phe Ser Gly His Ala Gly
             20                  25                  30

Arg Val Ile Glu Asn Pro Arg Glu Ala Leu Ser Val Ala Leu Glu Glu
         35                  40                  45

Ala Gln Ala Trp Arg Lys Lys Thr Asn His Arg Leu Ser Leu Pro Met
     50                  55                  60

Pro Ala Ser Gly Thr Ser Leu Ser Ala Ala Ile His Arg Thr Gln Leu
 65                  70                  75                  80

Trp Phe His Gly Arg Ile Ser Arg Glu Glu Ser Gln Arg Leu Ile Gly
                 85                  90                  95
```

```
Gln Gln Gly Leu Val Asp Gly Leu Phe Leu Val Arg Glu Ser Gln Arg
                100                 105                 110

Asn Pro Gln Gly Phe Val Leu Ser Leu Cys His Leu Gln Lys Val Lys
            115                 120                 125

His Tyr Leu Ile Leu Pro Ser Glu Glu Gly Arg Leu Tyr Phe Ser
        130                 135                 140

Met Asp Asp Gly Gln Thr Arg Phe Thr Asp Leu Leu Gln Leu Val Glu
145                 150                 155                 160

Phe His Gln Leu Asn Arg Gly Ile Leu Pro Cys Leu Leu Arg His Cys
                165                 170                 175

Cys Thr Arg Val Ala Leu
                180

<210> SEQ ID NO 25
<211> LENGTH: 43
<212> TYPE: PRT
<213> ORGANISM: mus muris

<400> SEQUENCE: 25

Pro Leu Arg Ser Val Ser Asp Asn Thr Leu Val Ala Met Asp Phe Ser
1               5                   10                  15

Gly His Ala Gly Arg Val Ile Asp Asn Pro Arg Glu Ala Leu Ser Ala
            20                  25                  30

Ala Met Glu Glu Ala Gln Ala Trp Arg Lys Lys
        35                  40

<210> SEQ ID NO 26
<211> LENGTH: 80
<212> TYPE: PRT
<213> ORGANISM: mus muris

<400> SEQUENCE: 26

Ser Arg His Leu Arg Leu Ser Tyr Leu Gly Ser Pro Pro Leu Arg Ser
1               5                   10                  15

Val Ser Asp Asn Thr Leu Val Ala Met Asp Phe Ser Gly His Ala Gly
            20                  25                  30

Arg Val Ile Asp Asn Pro Arg Glu Ala Leu Ser Ala Ala Met Glu Glu
        35                  40                  45

Ala Gln Ala Trp Arg Lys Lys Thr Asn His Arg Leu Ser Leu Pro Thr
    50                  55                  60

Thr Cys Ser Gly Ser Ser Leu Ser Ala Ala Ile His Arg Thr Gln Pro
65                  70                  75                  80

<210> SEQ ID NO 27
<211> LENGTH: 170
<212> TYPE: PRT
<213> ORGANISM: mus muris

<400> SEQUENCE: 27

Pro Leu Arg Ser Val Ser Asp Asn Thr Leu Val Ala Met Asp Phe Ser
1               5                   10                  15

Gly His Ala Gly Arg Val Ile Asp Asn Pro Arg Glu Ala Leu Ser Ala
            20                  25                  30

Ala Met Glu Glu Ala Gln Ala Trp Arg Lys Lys Thr Asn His Arg Leu
        35                  40                  45

Ser Leu Pro Thr Thr Cys Ser Gly Ser Ser Leu Ser Ala Ala Ile His
    50                  55                  60
```

```
Arg Thr Gln Pro Trp Phe His Gly Arg Ile Ser Arg Glu Glu Ser Gln
 65              70                  75                  80

Arg Leu Ile Gly Gln Gln Gly Leu Val Asp Gly Val Phe Leu Val Arg
                 85                  90                  95

Glu Ser Gln Arg Asn Pro Gln Gly Phe Val Leu Ser Leu Cys His Leu
            100                 105                 110

Gln Lys Val Lys His Tyr Leu Ile Leu Pro Ser Glu Asp Glu Gly Cys
            115                 120                 125

Leu Tyr Phe Ser Met Asp Glu Gly Gln Thr Arg Phe Thr Asp Leu Leu
    130                 135                 140

Gln Leu Val Glu Phe His Gln Leu Asn Arg Gly Ile Leu Pro Cys Leu
145                 150                 155                 160

Leu Arg His Cys Cys Ala Arg Val Ala Leu
                165                 170

<210> SEQ ID NO 28
<211> LENGTH: 182
<212> TYPE: PRT
<213> ORGANISM: mus muris

<400> SEQUENCE: 28

Ser Arg His Leu Arg Leu Ser Tyr Leu Gly Ser Pro Pro Leu Arg Ser
  1               5                  10                  15

Val Ser Asp Asn Thr Leu Val Ala Met Asp Phe Ser Gly His Ala Gly
                 20                  25                  30

Arg Val Ile Asp Asn Pro Arg Glu Ala Leu Ser Ala Ala Met Glu Glu
             35                  40                  45

Ala Gln Ala Trp Arg Lys Lys Thr Asn His Arg Leu Ser Leu Pro Thr
     50                  55                  60

Thr Cys Ser Gly Ser Ser Leu Ser Ala Ala Ile His Arg Thr Gln Pro
 65              70                  75                  80

Trp Phe His Gly Arg Ile Ser Arg Glu Glu Ser Gln Arg Leu Ile Gly
                 85                  90                  95

Gln Gln Gly Leu Val Asp Gly Val Phe Leu Val Arg Glu Ser Gln Arg
            100                 105                 110

Asn Pro Gln Gly Phe Val Leu Ser Leu Cys His Leu Gln Lys Val Lys
            115                 120                 125

His Tyr Leu Ile Leu Pro Ser Glu Asp Glu Gly Cys Leu Tyr Phe Ser
    130                 135                 140

Met Asp Glu Gly Gln Thr Arg Phe Thr Asp Leu Leu Gln Leu Val Glu
145                 150                 155                 160

Phe His Gln Leu Asn Arg Gly Ile Leu Pro Cys Leu Leu Arg His Cys
                165                 170                 175

Cys Ala Arg Val Ala Leu
                180
```

GRB14, GRB14 FUSION PROTEINS, AND SCREENING METHODS

The present invention relates to the use of the Grb14 protein and of homologous adapter proteins (proteins of the Grb7 family), as a tool for screening for molecules intended for treating diseases involving insulin.

Insulin, which is the principal hormone for the regulation of energy metabolism, is the only blood-glucose-lowering hormone in the body; it stimulates the transport of glucose and its use by peripheral tissues (skeletal muscles and adipose tissue) and inhibits the endogenous production of glucose by the liver.

Insulin acts through a receptor which is expressed at the plasma membrane of cells. This receptor is part of the family of receptors with tyrosine kinase activity, which are characterized by the presence of an intracellular domain which bears the catalytic activity. Binding of the ligand induces dimerization of the receptors, activation of the tyrosine kinase domain and phosphorylation (autoposphorylation and transphosphorylation) of specific tyrosine residues present in the cytosolic component of the receptors (Ullrich. A. et al. (1990) Cell, 61, 203–212).

The insulin receptor has the particularity of being present in a naturally dimerized form. The binding of the insulin to the extracellular α subunit induces conformation modifications which result in the activation of the kinase domain borne by the β subunit of the receptor, and in its autophosphorylation, which is required for complete activation of the receptor. The insulin receptor activated in this way phosphorylates intracellular proteins which are used as insulin signal effectors.

Specifically, the transduction of a signal inside the cell, after a receptor with tyrosine kinase activity has been stimulated, makes use of protein-protein interaction cascades which result in a metabolic or mitogenic effect, and in which the molecular adapters have a preferred role. Through their protein interaction domains, the adapters enable the recruitment of successive effectors, constituting the signalling pathways.

Among the various relays between the insulin receptor and its intracellular effectors, the most well characterized adapter proteins are IRS-1, IRS-2 (Insulin Receptor substrate-1 and 2) and Shc (Src and collagen homologous protein) (White M. F. et al. (1994) J. Biol. Chem., 269, 1–4; Waters S. B., et al. (1996) Trends Cell Biol., 6, 1–4). They are not specific for insulin-sensitive tissues and are also phosphorylated both after the activation of other tyrosine kinase receptors and after that of cytokine receptors or G protein-coupled receptors (Bonfini L. et al. (1996) Trends Biochem. Sci., 21, 257–261; Souza S. C. et al. (1994) J. Biol. Chem., 269, 30085–30088; Argetsinger L. S. et al. (1995) J. Biol. Chem., 270, 14685–14692; Platanias L. C. et al. (1996) J. Biol. Chem., 271, 278–282; Velloso L. A. et al. (1996) Proc. Natl. Acad. Sci. USA, 93, 12490–12495; Kowalski-Chauvel A. et al. (1996) J. Biol. Chem., 271, 26536–26361).

Thus for example, the Shc protein binds to the activated insulin receptor, is then phosphorylated and recruits the Grb2 adapter which binds to phosphotyrosine residues of Shc, through its SH2 domain, and binds, via an SH3 domain, to the nucleotide exchanger Sos, which will itself enable the activation of Ras (Schlessinger, J. (1993), Trends Bioch. Sci., 18, 273–275).

Recently, novel adapter proteins which may be specifically involved in insulin signal transduction have been cloned by interaction with the insulin receptor using the double-hybrid system, in particular various isoforms of the Grb10 protein from humans and from mice (Liu F. et al. (1995) Proc. Natl. Acad. Sci. USA, 92, 10287–10291; O'Neill T. J. et al. (1996) J. Biol. Chem., 271, 22506–22513; Frantz J. D. et al. (1997) J. Biol. Chem., 272, 2659–2667).

Even more recently, the inventors have cloned the rat rGrb14 and rGrb7 proteins by interaction with the insulin receptor using the double-hybrid system (Kasus-jacobi et al. (1998) J. Biol. Chem., 273, 26026–26035).

The mGrb10, hGrb10, hGrb14 and rGrb14 proteins belong to the same family of adapter proteins, the first known member of which is the Grb7 protein which binds to the receptor for EGF, for Ret and for PDGF (Margolis B. (1992) Proc. Natl. Acad. Sci. USA, 89, 8894–8898). Hereinafter, the proteins of this family are termed proteins of the Grb7 family.

These proteins which have been cloned by interaction with activated insulin receptors appear to play an important role in insulin signal transduction.

Thus, the inventors have shown that the expression of the rGrb14 protein is very well correlated with the sensitivity of tissues to insulin and that its overexpression in CHO-IR cells (Chinese Hamster Ovary cells expressing high levels of insulin receptors of human origin) inhibits the effects of insulin by decreasing the activation of IRS-1 without modifying the autophosphorylation of the insulin receptor (Kasus-Jacobi et al. (1998) already cited).

The adapter proteins of the Grb7 family are characterized by the succession of three domains:
 a proline-rich sequence named PP, close to the amino-terminal end,
 a central domain named PH (Pleckstrin homology) and
 a domain named SH2 (Src homology 2) at the carboxy-terminal end, known to interact with sequences containing phosphotyrosines (Ooi J. et al. (1995) Oncogene, 10, 1621–1630; Margolis B. (1992) already cited; Daly R. J. (1996) already cited).

Besides these domains which have already been studied in other proteins, the inventors have revealed a novel domain on the rGrb14 protein, named PIR (Phosphoxylated Insulin Receptor Interacting Region) corresponding to residues 340 to 437 of the protein; by comparison between the Grb7, Grb10 and Grb14 proteins, the inventors have shown that a 43 amino acid sequence corresponding to amino acids 365 to 470 of the rGrb14 protein is highly conserved throughout the family of these proteins (Kasus-Jacobi et al. (1998) already cited) and should play a specific role in the attachment of these proteins to the insulin receptor.

The PIR domain is homologous to the BPS domain (Between PH and SH2) (Kasus-Jacobi et al. (1998) already cited), recently demonstrated on the hGrb10 protein (He W. et al. (1998) J. Biol. Chem., 273, 6860–6867), and corresponds to amino acids 358–434 of the Grb14 protein.

The association between the activated insulin receptor and the proteins of the Grb7 family involves the two domains PIR and SH2. Depending on the Grb protein under consideration, the respective role of the two domains is more or less important. Specifically, it is essentially PIR which is responsible for the binding of Grb14 to the insulin receptor (Kasus-Jacobi et al. (1998) already cited), whereas PIR and SH2 are involved in the interaction between Grb10 and the receptor (He et al (1998) already cited).

Several teams have shown that there are defects in phosphorylation of the insulin receptor and also modifications of the effects of insulin on the transport of glucose and on the activation of certain enzymes in obese or diabetic patients (Arner, P. et al., J. N. (1987), Diabetologia, 30, 437–440; Caro, J. F. et al. (1987), J. Clin. Invest., 79, 1330–1337; Mandarino, L. J. (1989), Diab. Metab. Rev., 5, 475–486).

Mutations of the insulin receptor gene may lead, via various mechanisms, to a decrease in the tyrosine kinase activity of the receptor, thus contributing to the development of a condition of insulin resistance and to the institution of pathological conditions such as obesity and non-insulin-dependent diabetes (DNID) (Taylor, S. I. (1992), *Diabetes*, 41, 1473–1490).

In conditions of insulin resistance, hyperglycemia develops when the endogenous secretion of insulin is no longer sufficient, and it is necessary to resort to insulin therapy in order to maintain carbohydrate homeostasis. After the diabetes has evolved for 10 years, severe complications are observed in 30% of cases. These complications, which are secondary to poor control of glycemia, have various very serious clinical implications (renal failure, necrosis and amputation of the lower limbs, blindness) which lead to a shortening of the life expectancy of the patients.

Normalization of the tyrosine kinase activity, when it is disturbed, may be envisioned either directly, using molecules which act on this enzyme (Levitzki et al. (1995), *Science* 267, 1782–1788) or indirectly, by inhibiting the interactions between the adapter proteins and the tyrosine kinase (Pendergast et al. (1993), *Cell*, 75, 175–185).

Now, the inventors have shown, surprisingly, that the binding, to the activated insulin receptor, of the PIR domain of the proteins of the family of Grb7 proteins (Grb14, Grb10 and Grb7), alone or associated with the SH2 fragment (PIR–SH2), inhibits the tyrosine kinase activity of said receptor.

The subject of the present invention is the use of a fragment consisting of the PIR domain or the PIR–SH2 domain of a protein of the family of Grb7 proteins, as a tool for screening for molecules intended for treating diseases involving insulin.

According to an advantageous embodiment of said use, said fragment is selected from the group consisting of the sequences: SEQ ID NO: 1–28 which correspond, respectively, to PIR fragments (residues 365–407 and residues 353–436) and to PIR–SH2 fragments (residues 365–538 and residues 353–538) of the rGrb14, hGrb14, mGrb10, hGrb10, rGrb7, hGrb7 and mGrb7 proteins.

For the purposes of the present invention, the numbering of the residues of the protein fragments is given with reference to the sequence of the rGrb14 protein after alignment.

Interestingly, the inventors have shown that the inhibitory effect of the Grb14 protein is reproduced by the purified GST-PIR and GST-PRI+SH2 fusion proteins, which are obtained by fusion of GST with the PIR domain or the PIR+SH2 domain of rGrb14. On the other hand, this inhibitory effect is not observed with the GST-SH2 fusion protein obtained by GST fusion with the SH2 domain of rGrb14.

Unexpectedly, the inventors have shown that the PIR domain alone has an activity equivalent to that of the whole protein, whereas the PIR+SH2 domain has a much greater inhibitory effect than PIR expressed alone. Specifically, total inhibition of the tyrosine kinase activity of the insulin receptors is obtained when 0.3 µg of GST-PIR protein is added, whereas only 0.03 µg of GST-PIR+SH2 is necessary. It appears, therefore, that, while the SH2 domain has no inhibitory activity per se, on the other hand it greatly potentiates the effect of PIR.

In comparable fashion, the inventors have shown that the PIR and PIR+SH2 domains of Grb10 have an inhibitory effect on the tyrosine kinase activity of the insulin receptor. The SH2 domain of Grb10 does not, in itself, have an inhibitory effect, but it too potentiates the inhibition induced by PIR.

In addition, the inventors have shown that the insulin receptor is more sensitive to the inhibitory effect of Grb14 than to that of Grb10 and of Grb7, and that the effect may be obtained both with the whole protein and with the PIR domain or the PIR–SH2 domain.

The PIR and PIR–SH2 domains of the Grb14, Grb10 and Grb7 proteins therefore behave like endogenous inhibitors of the tyrosine kinase activity of the insulin receptor, which is an entirely novel function for molecular adapters. In fact, unlike the adapter proteins IRS-1, IRS-2 or Shc which are intermediates between the insulin receptor and cellular effectors, said domains of the proteins of the Grb7 family act directly on the tyrosine kinase activity of the insulin receptor.

Consequently, the PIR and PIR–SH2 domains of the Grb14 protein and of the homologous adapter proteins (proteins of the Grb7 family) constitute potential targets for medicinal products.

Specifically, compounds which are capable of increasing or of suppressing the interactions of the domains of said proteins may prevent or cure disorders of the organism which are related to a modification of the activity of the kinase protein of the insulin receptor.

Consequently, the present invention therefore also relates to a method for detecting molecules capable of stimulating or inhibiting (modulating) the tyrosine kinase activity of the insulin receptor, characterized in that it comprises:
a) bringing the activated insulin receptor into contact with a fragment consisting of the PIR domain or the PIR–SH2 domain of a protein of the family of Grb7 proteins, and the molecule to be tested, under conditions which allow binding of said fragment to said receptor,
b) adding a tyrosine kinase substrate,
c) measuring the tyrosine kinase activity, and
d) determining the modulation (inhibition or stimulation) of the tyrosine kinase activity by comparison with a control consisting of the activated insulin receptor and said fragment.

In accordance with the invention, said fragment is preferably selected from the group consisting of the sequences SEQ ID NO: 1 to 28.

According to an advantageous embodiment of said method, prior to step a) above, a preselection of the molecules, capable of stimulating or inhibiting (modulating) the interactions of a fragment consisting of the PIR domain or the PIR–SH2 domain of a protein of the family of Grb7 proteins, with the insulin receptor, is carried out by:
1) immobilizing said fragment on a solid support,
2) bringing the molecule to be tested into contact with said fragment, then
3) incubating with the labeled and pre-activated insulin receptor, under conditions which allow binding of said receptor to said fragment,
4) separating said labeled receptor not retained on the support,
5) detecting the complex possibly formed between said fragment and the activated insulin receptor, and
6) determining the effect of the molecule (inhibition or stimulation of the fragment-receptor interaction), by comparison with a control comprising said fragment and the insulin receptor.

In order to allow said fragment to be immobilized on a solid support, said fragment may, for example, be expressed as a fusion with a protein such as GST.

Said receptor may, for example, be labeled with a radioactive molecule or fused to a fluorescent protein such as GFP (Green Fluorescent Protein).

When said receptor is labeled with a fluorescent or radioactive molecule, the interaction between said fragment and said receptor is detected by reading the fluorescence or the radioactivity retained on the solid support.

A subject of the present invention is also the use of a molecule capable of binding to a fragment consisting of the PIR domain or the PIR–SH2 domain of a protein of the family of Grb7 proteins, and of inhibiting the tyrosine kinase activity of the insulin receptor, for manufacturing a medicinal product which can be used in the treatment of diseases involving insulin, in particular diabetes and obesity.

According to an advantageous embodiment of said use, said molecule is obtained using the method in accordance with the invention.

The compounds selected in this way can potentially be used for preventing or treating diseases involving insulin, such as for example diabetes and obesity or other pathological conditions characterized by insulin resistance, such as polycystic ovary syndrome (Legro, R. S. et al. (1998), *Rec. Progr. Hormone Res.*, 53, 217–255) or syndrome X (Komers, R. et al., (1998), *Physiol. Res.*, 47, 215–225).

Besides the arrangements above, the invention also comprises other arrangements which will emerge from the following description, which refers to examples of implementation of the method which is the subject of the present invention and also to the attached diagrams, in which:

FIG. 1 illustrates the alignment of the proteins of the family of Grb proteins. The percentages of amino acid identity of the domains are expressed relative to the homologous domain of rGrb14. PP: motif rich in proline residues, binding site for proteins containing SH3 domains; PH: pleckstrin homology domain, association with phospholipids or proteins; PIR phosphorylated insulin receptor interacting region; SH2: domain allowing interaction with phosphotyrosine residues.

FIG. 2 illustrates the alignment of the sequences of the PIR domain of the proteins of the family of Grb proteins: rGrb14 (SEQ ID NO: 2), hGrb14 (SEQ ID NO: 6), hGrb10 (SEQ ID NO: 14) and hGrb7 (SEQ ID NO: 22). The numbering of the amino acids is given with reference to the sequence of the rGrb14 protein. The conserved amino acids are indicated with an asterisk. The conserved domain corresponding to residues 365–407 of the rGrb14 (SEQ ID NO: 1), hGrb14 (SEQ ID NO: 5), hGrb10 (SEQ ID NO: 13) and hGrb7 (SEQ ID NO: 21) proteins is in gray.

FIG. 3 illustrates the sequence of the PIR–SH2 domains of the proteins of the family of Grb proteins: rGrb14, hGrb10 and hGrb7. The complete sequence of the PIR–SH2 domain (residues 353–538) of rGrb14 (SEQ ID NO: 4), hGrb10 (SEQ ID NO: 16) and hGrb7 (SEQ ID NO: 24) is given. The sequence of fragment 405–538 of the PIR–SH2 domain of rGrb14 (SEQ ID NO: 3), hGrb10 (SEQ ID NO: 15) and hGrb7 (SEQ ID NO: 23) is underlined.

Figure 4:
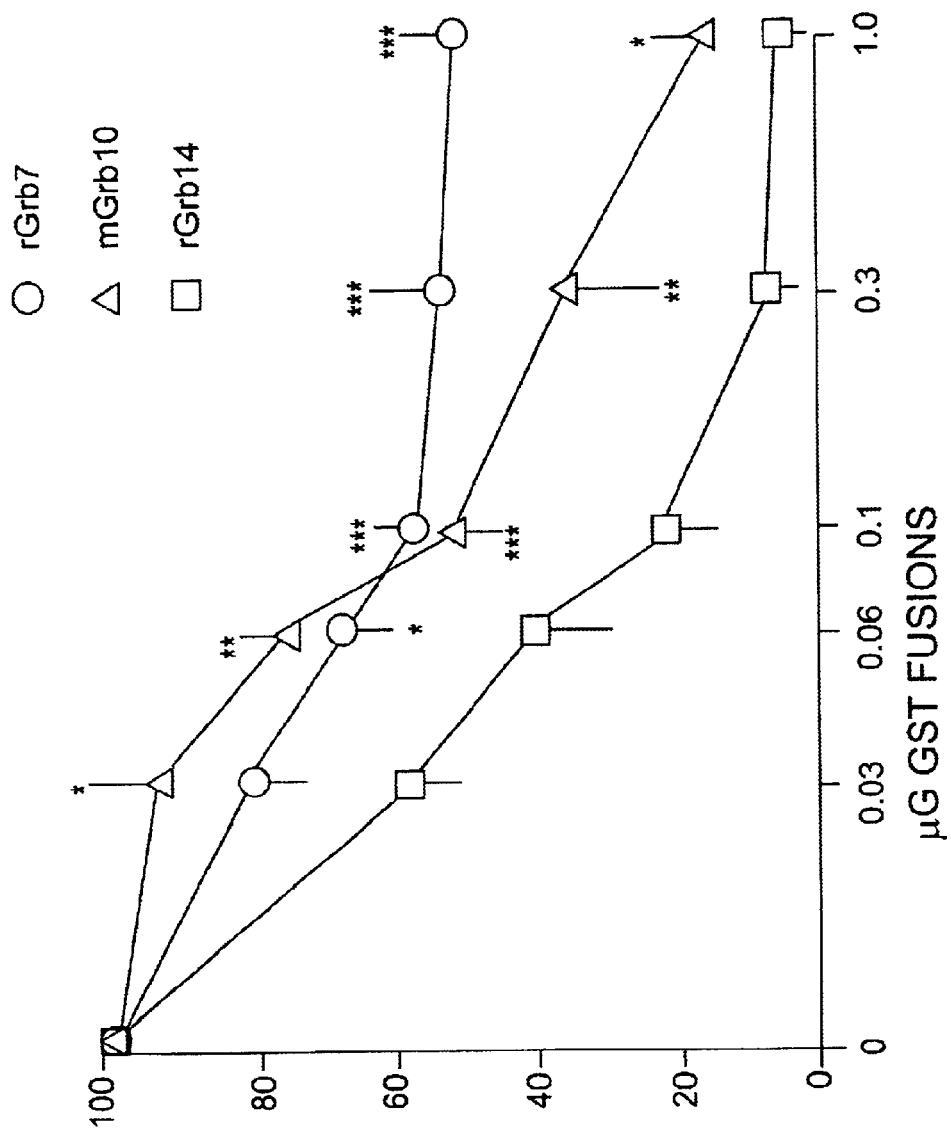

FIG. 4 illustrates the effect of the Grb proteins on the tyrosine kinase activity of insulin receptors; (●) GST-rGrb14; (▲) GST-mGrb10; (■) GST-rGrb7. The results are expressed as the percentage of the value obtained in the absence of added protein. Number of experiments=4. The effects of the GST-mGrb10 and GT-rGrb7 proteins compared with those of the GST-rGrb14 protein show statistically significant differences, indicated by * for p<0.05,  for p<0.01 and * for p<0.001.

Figure 5:
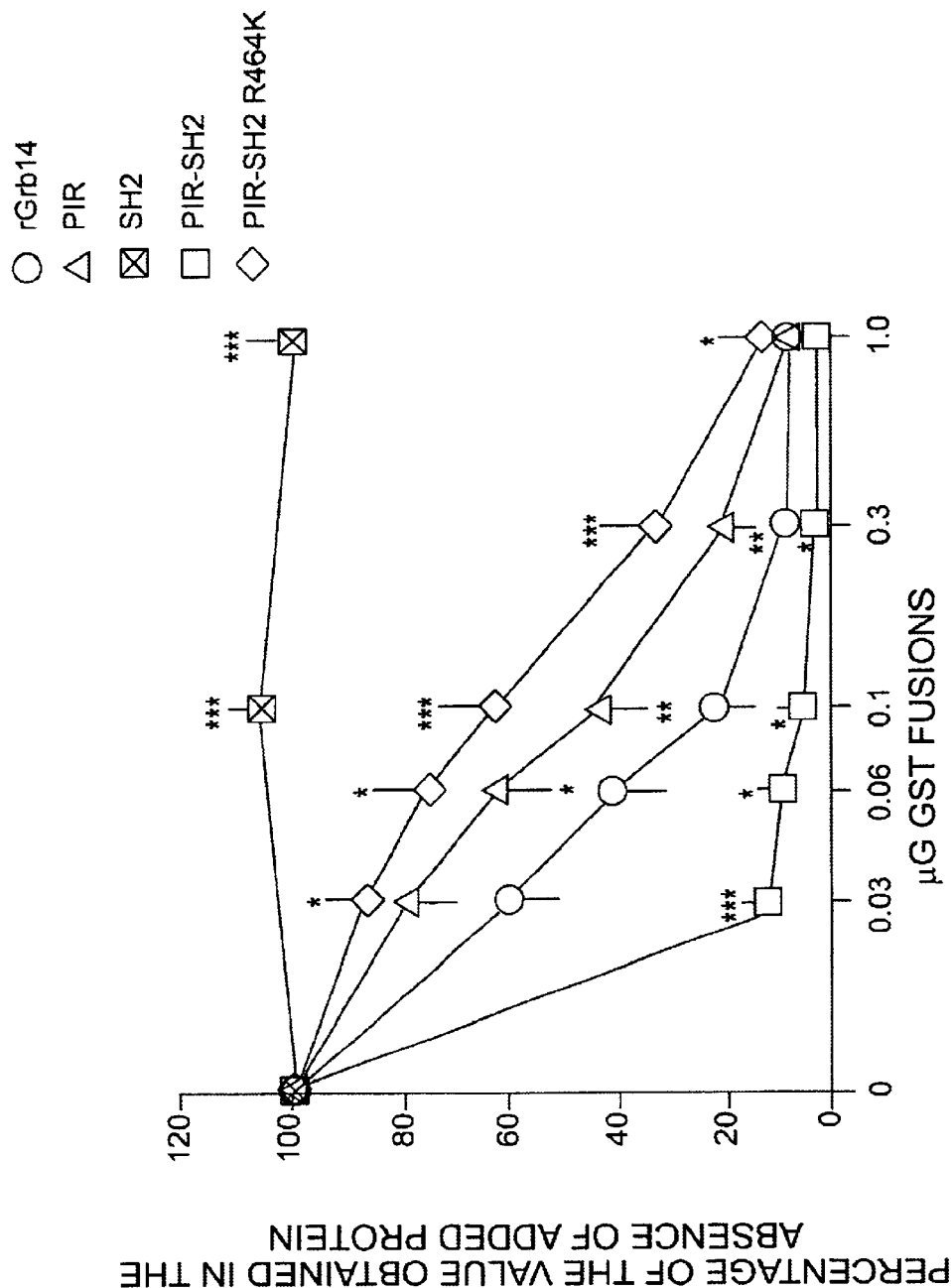

FIG. 5 illustrates the inhibition of the tyrosine kinase activity of insulin receptors by the rGrb14 protein: (●) GST-rGrb14; (▲) GST-PIR of rGrb14; (☒) GST-SH2 of rGrb14; (■) GST-PIR+SH2 of rGrb14; (◇) GST-PIR+SH2 R464K of rGrb14. The results are expressed as the percentage of the value obtained in the absence of added protein. Number of experiments=5. The effects of the various rGrb14 constructs compared with those of the whole GST-rGrb14 protein show statistically, significant differences, indicated by * for p<0.05,  for p<0.01 and * for p<0.001.

Figure 6:
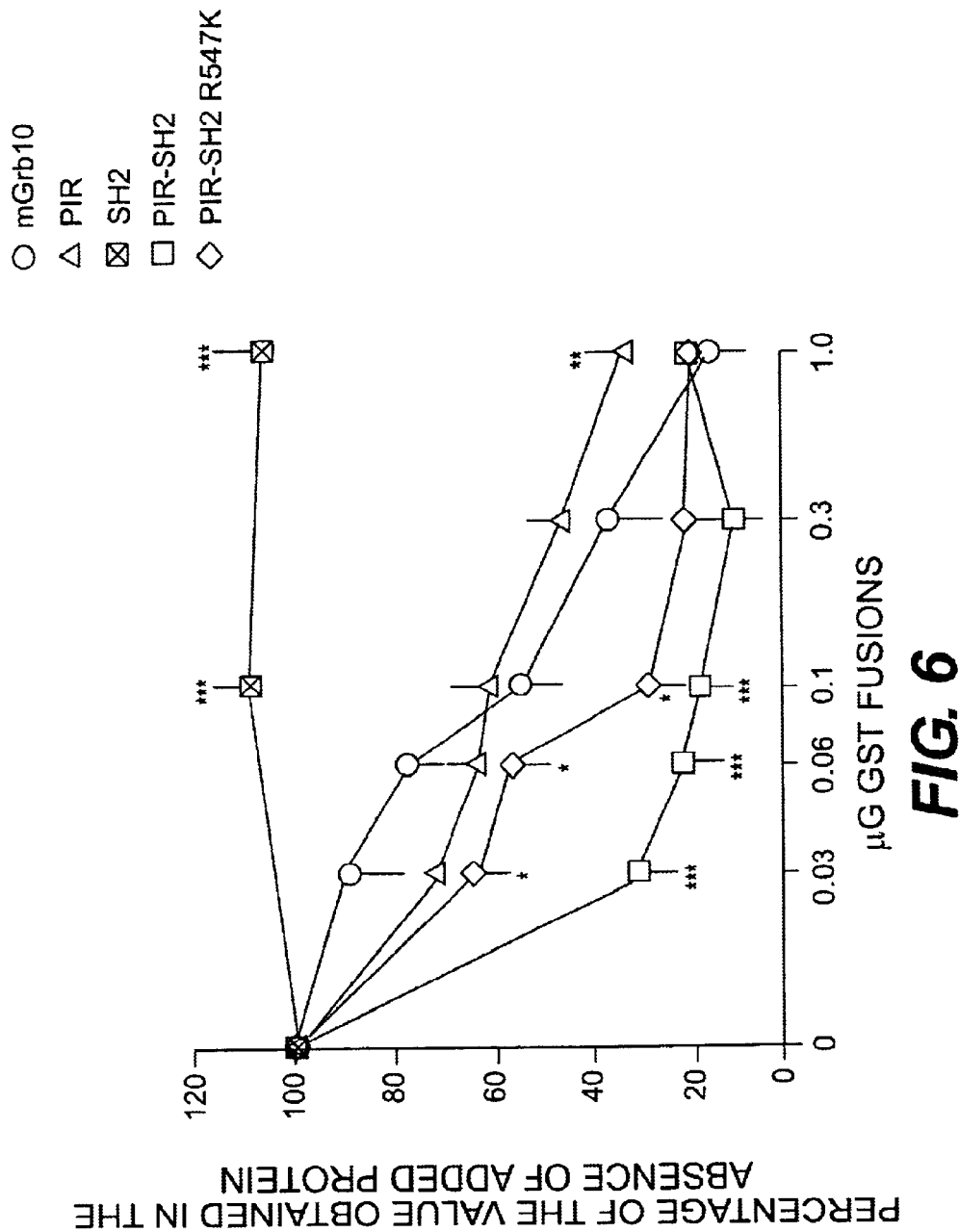

FIG. 6 illustrates the inhibition of the tyrosine kinase activity of insulin receptors by the various domains of mGrb10: (●) GST-mGrb10; (▲) GST-PIR of mGrb10; (☒) GST-SH2 of mGrb10; (■) GST-PIR+SH2 of mGrb10; (◇) GST-PIR+SH2 R547K of mGrb10. The results are expressed as a percentage of the value obtained in the absence of added protein. Number of experiments=4. The effects of the various mGrb10 constructs compared with those of the whole GST-mGrb10 protein show statistically significant differences, indicated by: * for p<0.05,  for p<0.01 and * for p<0.001.

FIG. 7 illustrates the inhibition of the tyrosine kinase activity of insulin receptors by the various domains of rGrb7: (●) GST-rGb7; (▲) GST-PIR of rGb7; (☒) GST-SH2 of rGrb7; (■) GST-PIR+SH2 of rGrb7. The results are expressed as a percentage of the value obtained in the absence of added protein. Number of experiments=2. The effects of the various rGrb7 constructs compared with those of the whole GST-rGrb7 protein show statistically significant differences, indicated by: * for p<0.05,  for p<0.01 and * for p<0.001.

EXAMPLE 1

Comparison of the Effect of the rGrb14, mGrb10 and rGrb7 Proteins on the Tyrosine Kinase Activity of Insulin Receptors 1. Procedure:

Insulin receptors are partially purified from CHO-IR cells by passing a cell lysate over a weak germ lectin column and eluting the glycoproteins retained with 0.3 M N-acetylglucosamine. The insulin receptors thus purified are incubated in the presence of insulin (0 or $10^{-7}$ M) for 1 hour at room temperature. A buffer containing 20 $\mu$M ATP, $MnCl_2$ and $MgCl_2$ ions and [$\gamma$-$^{32}$P] ATP is then added so as to allow the receptors to autophosphorylate, as are increasing amounts of the purified Grb proteins expressed as a fusion with GST. 30 minutes later, 15 $\mu$g of a synthetic substrate, poly Glu-Tyr (4:1), are added. The tyrosine kinase activity of the receptors is measured by the incorporation of radioactivity into the poly Glu-Tyr during 30 min.

2. Results:

They are represented in FIG. 4.

The addition of the GST-rGrb14 and GST-mGrb10 fusion proteins induces dose-dependent inhibition of the tyrosine kinase activity of the insulin receptors, and the highest concentrations allow total inhibition of the enzyme. By comparison, the GST-rGrb7 protein enables a maximum of only 40% inhibition. The dose-response curve of the effect of GST-mGrb10 is shifted to the right compared to the curve of the effect of GST-rGrb14. 50% inhibition of the tyrosine kinase activity of the receptors is obtained when using, respectively, 0.04 $\mu$g of GST-rGrb14 and 0.13 $\mu$g of GST-mGrb10. The tyrosine kinase activity of the insulin receptors is therefore more sensitive to the inhibitory effect of rGrb14 than to that of mGrb10.

These results show that the Grb proteins have inhibitory activity on the tyrosine kinase activity of insulin receptors and that the rGrb14 protein has the greatest inhibitory effect.

EXAMPLE 2

Inhibitory Effect of the Various Domains of rGrb14 on the Tyrosine Kinase Activity of Insulin Receptors 1. Procedure:

The insulin receptors are partially purified as described in Example 1. The various domains of rGrb14 (rGrb14, PIR, SH2, PIR+SH2, PIR+SH2 R464K) are produced as a fusion with GST and purified. The inhibitory effect of these proteins on the tyrosine kinase activity of insulin receptors is analyzed as described in Example 1.

2. Results:

They are as represented in FIG. 5.

The PIR domain exerts an inhibitory effect comparable to that of the whole rGrb14 protein, whereas the SH2 domain has no effect (in the same way as the protein deleted of the PIR+SH2 regions, results not shown). However, the PIR+SH2 domain has a much greater inhibitory effect than PIR alone or the whole protein (the maximum inhibitory effect is obtained by adding 0.03 μg of protein). This potentiation is suppressed by mutating the arginine 464 residue of the conserved FLVRES motif, which inactivates the SH2 domain, since the PIR+SH2 R464K domain has the same effect as PIR alone.

These results show that the inhibitory effect of rGrb14 on the tyrosine kinase activity of insulin receptors is due to the presence of PIR. The SH2 domain alone has no effect, but it potentiates the PIR effect.

EXAMPLE 3

Inhibitory Effect of the Various Domains of mGrb10 on the Tyrosine Kinase Activity of Insulin Receptors 1. Procedure:

The procedure is identical to that described in Example 2.

2. Results:

They are represented in FIG. 6.

The PIR domain exerts an inhibitory effect comparable to that exerted by the whole protein. The SH2 domain alone has no inhibitory action, but it potentiates the inhibition exerted by PIR (the dose-response curve of PIR+SH2 is shifted to the left). Mutating the arginine residue of the FLLRDS motif of the SH2 domain inhibits the potentiating effect of the PIR+SH2 domain (PIR+SH2 R547K mutant).

These results show that the PIR or PIR–SH2 domains of rGrb14 have a greater inhibitory effect than the PIR or PIR–SH2 domains of mGrb10.

EXAMPLE 4

Inhibitory Effect of the Various Domains of rGrb7 on the Tyrosine Kinase Activity of the Insulin Receptors 1. Procedure:

The procedure is identical to that described in Example 2.

2. Results:

They are represented in FIG. 7.

The PIR domain exerts an inhibitory effect comparable to that exerted by the whole protein. The SH2 domain alone has no inhibitory action, but it potentiates the inhibition exerted by PIR (the dose-response curve of PIR+SH2 is shifted to the left). The PIR and PIR–SH2 domains of rGrb7 have a lesser inhibitory effect compared to that of the PIR and PIR–SH2 domains of the rGrb14 and mGrb10 proteins.

As emerges from the above, the invention is in no way limited to its methods of implementation, preparation and application which have just been described more explicitly; on the contrary, it encompasses all of the variants thereof which may occur to a person skilled in the art, without departing from the context or scope of the present invention.

What is claimed is:

1. A fragment of the PIR domain of the protein hGrb14 consisting of the sequence SEQ ID NO: 5 or SEQ ID NO: 6.

2. A fusion protein comprising the fragment of claim 1.

3. A method for detecting in vitro molecules capable of modulating the tyrosine kinase activity of the insulin receptor, comprising:

a) bringing an activated insulin receptor into contact with the fusion protein of claim 2, and the molecule to be tested, under conditions which allow binding of said fragment to said receptor, b) adding a tyrosine kinase substrate, c) measuring the tyrosine kinase activity, and d) determining the modulation of the tyrosine kinase activity by comparison with a control consisting of the activated insulin receptor and said fragment.

4. The method of claim 3 further comprising preselection prior to step a) wherein molecules capable of modulating the interactions of a fragment of the PIR domain of the protein hGrb14 with the insulin receptor are identified, wherein said fragment consists of the sequence SEQ ID NO: 5 or SEQ ID NO: 6, said preselection comprising:

a) immobilizing said fragment on a solid support, b) bringing the molecule to be tested into contact with said fragment, then c) incubating with a labeled and pre-activated insulin receptor, under conditions which allow binding of said receptor to said fragment, d) separating said labeled receptor not retained on the support, e) detecting the complex possibly formed between said fragment and said activated insulin receptor, and f) determining the effect of the molecule by comparison with a control comprising said fragment and said insulin receptor absent the molecule to be detected.

5. A method for detecting in vitro molecules capable of modulating the tyrosine kinase activity of the insulin receptor, comprising:

a) bringing an activated insulin receptor into contact with a fragment of the PIR domain of the protein hGrb14, wherein said fragment consists of the sequence SEQ ID NO: 5 or SEQ ID NO: 6, and the molecule to be tested, under conditions which allow binding of said fragment to said receptor, b) adding a tyrosine kinase substrate, c) measuring the tyrosine kinase activity, and d) determining the modulation of the tyrosine kinase activity by comparison with a control consisting of the activated insulin receptor and said fragment.

6. The method of claim 5 further comprising preselection prior to step a) wherein molecules capable of modulating the interactions of a fragment of the PIR domain of the protein hGrb14 with the insulin receptor are identified, wherein said fragment consists of the sequence SEQ ID NO: 5 or SEQ ID NO: 6, said preselection comprising:

a) immobilizing said fragment on a solid support, b) bringing the molecule to be tested into contact with said fragment, then c) incubating with a labeled and pre-activated insulin receptor, under conditions which allow binding of said receptor to said fragment, d) separating said labeled receptor not retained on the support, e) detecting the complex possibly formed between said fragment and said activated insulin receptor, and f) determining the effect of the molecule by comparison with a control comprising said fragment and said insulin receptor absent the molecule to be detected.

* * * * *